(12) United States Patent
Sendai

(10) Patent No.: US 7,181,265 B2
(45) Date of Patent: Feb. 20, 2007

(54) FLUORESCENT IMAGE OBTAINING APPARATUS

(75) Inventor: Tomonari Sendai, Kaisei-machi (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 624 days.

(21) Appl. No.: 10/000,956

(22) Filed: Dec. 4, 2001

(65) Prior Publication Data

US 2002/0085753 A1 Jul. 4, 2002

(30) Foreign Application Priority Data

Dec. 4, 2000  (JP) .............................. 2000-368029

(51) Int. Cl.
*A61B 6/00* (2006.01)
(52) U.S. Cl. .................. 600/476; 600/473; 600/477; 600/478
(58) Field of Classification Search ........ 600/476–478, 600/473, 160, 178, 310, 180–182; 250/216, 250/458.1
See application file for complete search history.

(56) References Cited

U.S. PATENT DOCUMENTS

| 5,421,337 | A | * | 6/1995 | Richards-Kortum et al. ........................ 600/477 |
| 5,813,987 | A | * | 9/1998 | Modell et al. .............. 600/473 |
| 6,364,829 | B1 | * | 4/2002 | Fulghum ..................... 600/160 |

FOREIGN PATENT DOCUMENTS

| WO | WO 88/08272 A1 | 11/1988 |
| WO | WO 95/26673 A2 | 10/1995 |
| WO | WO 98/29050 A2 | 7/1998 |
| WO | WO 99/53832 A1 | 10/1999 |
| WO | WO 00/15101 A1 | 3/2000 |
| WO | WO 00/42910 A1 | 7/2000 |

\* cited by examiner

*Primary Examiner*—Brian L. Casler
*Assistant Examiner*—Baisakhi Roy
(74) *Attorney, Agent, or Firm*—Sughrue Mion, PLLC

(57) ABSTRACT

A fluorescent image obtaining apparatus for obtaining as an image the data relating to the fluorescent light emitted from a measurement portion upon the irradiation thereof by an excitation light, wherein by amplifying only the intensity of the fluorescent light, the S/N ratio of the fluorescent image based thereon is improved, is provided. The statistical quantities of a fluorescent image obtained by a wide-band fluorescent image obtaining element and a narrow-band fluorescent image obtaining element are computed by a statistical quantity computing means. If the statistical quantity is smaller than a predetermined value, the magnification rate of the imaging optical system is controlled by a magnification rate control means so that the fluorescent image is reduced and focused on the wide-band fluorescent image obtaining element and the narrow-band fluorescent image obtaining element.

34 Claims, 6 Drawing Sheets

F I G . 1
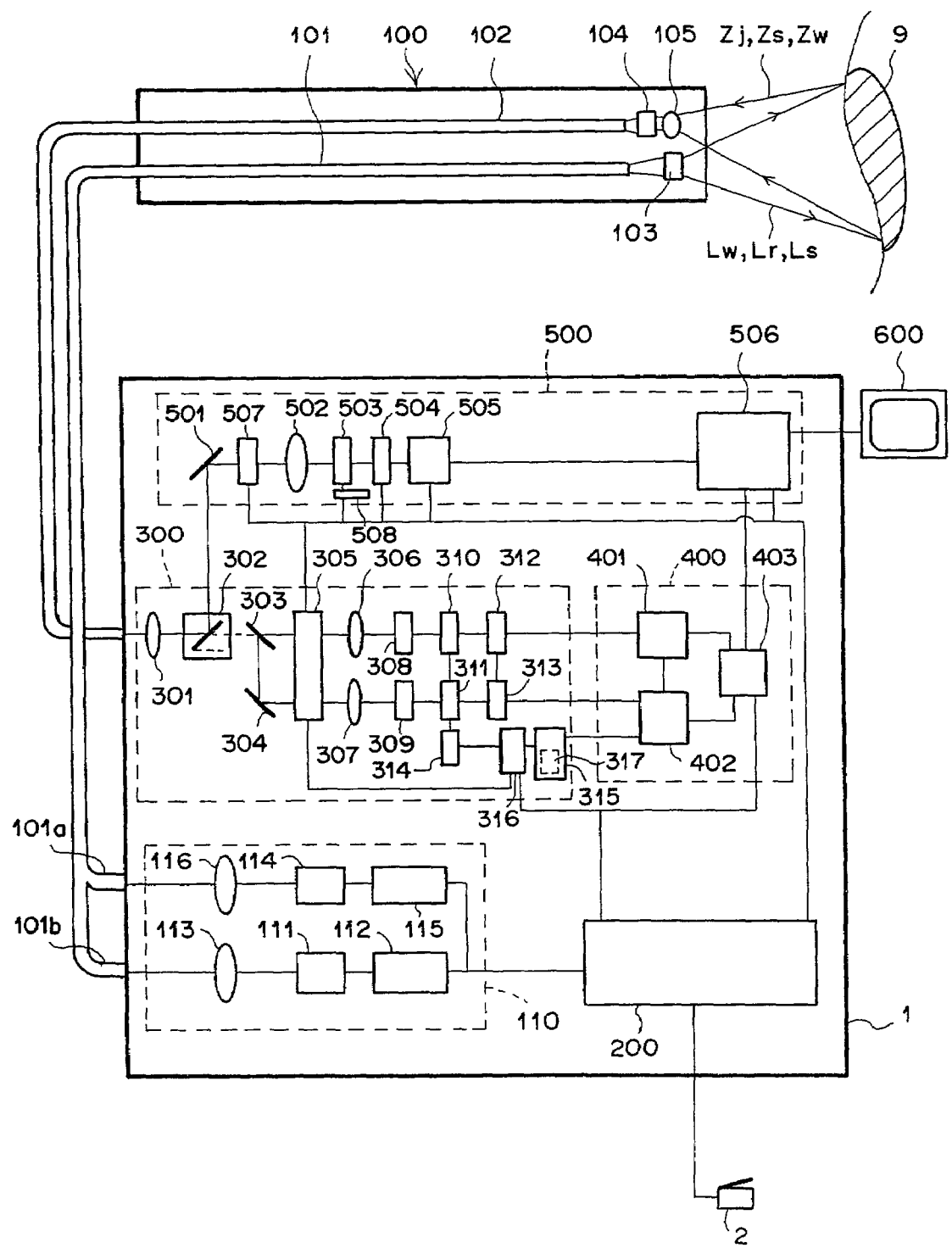

FLUORESCENT IMAGE OBTAINING APPARATUS

BACKGROUND OF THE INVENTION

1. Field of the Invention

The present invention relates to a fluorescent image obtaining apparatus for obtaining an image formed of the fluorescent light emitted from a measurement area upon the irradiation thereof by an excitation light, and which represents the data relating to a living-tissue subject.

2. Description of the Related Art

Fluorescent-light detection apparatuses have been proposed that make use of the fact that the intensity of the fluorescent light emitted from a normal tissue differs from the intensity of the fluorescent light emitted from a diseased tissue when a target subject is irradiated by an excitation light having a wavelength within the wavelength range of the intrinsic fluorophores of the target subject, wherein, by detecting the fluorescent light emitted from a target subject upon irradiation thereof by a excitation light having a wavelength within the wavelength range of the intrinsic fluorophores of the target subject, the location and range of penetration of a diseased tissue is discerned.

Normally, when a target subject is irradiated by a excitation light, because a high-intensity fluorescent light is emitted from a normal tissue, as shown by the solid line in FIG. 6, and a weak-intensity fluorescent light is emitted from a diseased tissue, as shown by the broken line in FIG. 6, by measuring the intensity of the fluorescent light emitted from aforementioned target subject, it can be determined whether the target subject is in a normal or a diseased state.

Further, methods have been proposed wherein the fluorescent light emitted upon the irradiation of a target subject by the excitation light is obtained as an image by a obtaining element or the like, and displayed as a fluorescent image corresponding to the intensity of the fluorescent-light. Further, according to the technology described above, because there is unevenness on the surface of a target subject, the intensity of the excitation light irradiating the target subject is not of a uniform intensity. Further, although the intensity of the fluorescent-light emitted from the target subject is substantially proportional to the intensity of the excitation light, the intensity of aforementioned excitation light becomes weaker in inverse proportion to the square of the distance between the excitation light and the target subject. Therefore, there are cases in which the fluorescent-light received from a diseased tissue located at a position closer to the excitation light source than a normal tissue is of a higher intensity than the fluorescent-light received from aforementioned normal tissue, and the state of the tissue of the target subject under examination cannot be accurately discerned based solely on the data relating to the intensity of the fluorescent-light received from the target subject upon the irradiation thereof with a excitation light. In order to remedy the problems described above, methods such as dividing two types of fluorescent-light intensities obtained of different wavelength ranges (a narrow-band near the 480 nm wavelength, and a wide band near the 430–730 nm wavelength range) to obtain the ratio therebetween, and displaying a computed-image based on the factor obtained thereby have been proposed. That is to say: an image display method of displaying an image based on the difference in the form of the fluorescent-light spectra reflecting the tissue-state of a target subject; a method of displaying a fluorescent image comprising detecting the intensity of the reflected-light reflected from a target subject upon the irradiation thereof with a reference-light composed of light in the near-infrared spectrum, which shows uniform absorption characteristics for awide variety of target subjects; obtaining the ratio between the intensity of the reference-light and the intensity of the fluorescent-light by division; and displaying a computed-image based on the factor obtained thereby; that is, methods such as obtaining a value reflecting the yield of the fluorescent-light and displaying an image; have been proposed. Further: a method of assigning color data to the factor obtained by dividing the intensities of the fluorescent light of different wavelength bands or to the factor obtained by dividing the intensity of the fluorescent light by the intensity of the reflected-light reflected from the target subject upon the irradiation thereof by the reference-light, and displaying an image representing the tissue-state of the target subject based on the difference in the colors thereof; a method of displaying a composite-image, which is an image imparting a sense of the surface roughness and which also reflects the tissue form of the target subject, formed by combining a color image based on said difference in color representing the tissue-state and a brightness image obtained by assigning brightness data to the intensity of the reflected-light reflected from the target subject upon the irradiation thereof by the reference-light; etc., have been proposed.

However, according to the technology described above, because the intensity of the fluorescent light emitted from the target subject is extremely weak, the S/N ratio of an image based on this fluorescent light is extremely poor. Accordingly, to date, a method for controlling the gain of an amplifying obtaining element for amplifying the intensity of the fluorescent light has been proposed as a method of improving the S/N ratio of a fluorescent image obtained based thereupon; however, according to this method, the intensity of the noise is amplified together with the intensity of the fluorescent light. Further, a method of changing the binning size of the obtaining element to an active binning size corresponding to detected fluorescent light has also been proposed, however, according to this method, although the intensity of the fluorescent light is amplified, because the dark noise of the peripheral pixels is also amplified when the pixels are coupled, the resulting S/N ratio is insufficient. Still further, there is a drawback in that the drive circuit of the obtaining element for changing the binning size is complicated.

SUMMARY OF THE INVENTION

The present invention has been developed in view of the circumstances described above, and it is a primary objective of the present invention to provide a fluorescent image obtaining apparatus capable of improving, by amplifying only the intensity of the fluorescent light, the S/N ratio of a fluorescent image based thereupon.

The first fluorescent image obtaining apparatus according to the present invention comprises: an illuminating means for guiding an excitation light to an area of which a measurement is to be taken (hereinafter referred to as a measurement area) and illuminating the measurement area with the excitation light; an image obtaining means for obtaining a fluorescent image based on the fluorescent light emitted from the measurement area upon the illumination thereof by the excitation light and which has been passed through an imaging optical system; and a readout means for reading out an image signal based on the fluorescent image obtained by the image obtaining means; further provided with a statistical quantity computing means for computing a statistical quantity based on the image signal of a predetermined region of the fluorescent image obtained by the image obtaining means; wherein the image obtaining means is provided with a magnification control means for determining the size of the fluorescent image by controlling, based on the statistical quantity, the magnification rate of the imaging optical system.

Further, the first fluorescent image obtaining apparatus according to the present invention can also be provided with an image processing means for subjecting the image signal read out by the readout means to a predetermined image process, and the image processing means can perform image processes on the image signal of a predetermined valid range within a predetermined region.

Still further, the first fluorescent image obtaining apparatus according to the present invention can also be provided with a display means for displaying a target-subject image based on the image signal read out by the readout means, and the display means can display a target-subject image based on the image signal of a predetermined valid range, which has been subjected to an image process by the image processing means.

In addition, the first fluorescent image obtaining apparatus according to the present invention can also be provided with a display magnification rate control means for controlling the magnification rate so that the target-subject image based on the image signal of the predetermined valid range is displayed at a predetermined size.

Additionally, the readout means can be a means for reading out only the image signal of a predetermined valid range of the fluorescent image.

The second fluorescent image obtaining apparatus according to the present invention comprises: an illuminating means for guiding an excitation light and an illuminating-light to a measurement area and illuminating the measurement area with the excitation light and the illuminating-light; an image obtaining means for obtaining a fluorescent image based on the fluorescent light emitted from the measurement area upon the illumination thereof by the excitation light and which has been passed through an imaging optical system, and a reflectance image based on the reflected-light reflected from the measurement area upon the illuminating thereof by the illuminating-light and which has been passed through an imaging optical system; and a readout means for reading out an image signal based on the fluorescent image and an image signal based on the reflectance image obtained by the image obtaining means; further provided with a statistical quantity computing means for computing a statistical quantity based on the image signal of a predetermined region of the fluorescent image obtained by the image obtaining means; wherein the image obtaining means is provided with a magnification control means for determining the size of the fluorescent image and the reflectance image by controlling, based on the statistical quantity, the magnification rate of the imaging optical system.

Further, the second fluorescent image obtaining apparatus according to the present invention can also be provided with an image processing means for subjecting the image signal read out by the readout means to a predetermined image process, and the image processing means can perform image processes on the image signal of a predetermined valid range of the predetermined region within a fluorescent image and the image signal corresponding thereto within the reflectance image.

Still further, the second fluorescent image obtaining apparatus according to the present invention can also be provided with a display means for displaying a target-subject image based on the image signal read out by the readout means, and the display means can display a target-subject image based on the aforementioned image signals of a predetermined valid range of the fluorescent image and the reflectance image, which have been subjected to image processes by the image processing means.

In addition, the second fluorescent image obtaining apparatus according to the present invention can also be provided with a display magnification rate control means for controlling the display magnification rate so that the target-subject image based on the image signal of the predetermined valid range is displayed at a predetermined size.

Additionally, the readout means can be a means for reading out only the image signals of a predetermined valid range of the fluorescent image and the reflectance image.

The third fluorescent image obtaining apparatus according to the present invention comprises: an illuminating means for guiding an excitation light and a reference-light to a measurement area and illuminating the measurement area with the excitation light and the reference-light; an image obtaining means for obtaining a fluorescent image based on the fluorescent light emitted from the measurement area upon the illumination thereof by the excitation light and which has been passed through an imaging optical system, and a reflected image based on the reflected-light reflected from the measurement area upon the illuminating thereof by the reference-light and which has been passed through an imaging optical system; and a readout means for reading out an image signal based on the fluorescent image and an image signal based on the reflected image obtained by the image obtaining means; further provided with a statistical quantity computing means for computing a statistical quantity based on the image signal of a predetermined region of the fluorescent image or the reflected image obtained by the image obtaining means; wherein the image obtaining means is provided with a magnification control means for determining the size of the fluorescent image and the reflected image by controlling, based on the statistical quantity, the magnification rate of the imaging optical system.

Further, the third fluorescent image obtaining apparatus according to the present invention can also be provided with an image processing means for subjecting the image signal read out by the readout means to a predetermined image process, and the image processing means can perform image processes on the image signal of a predetermined valid range of the predetermined region within a fluorescent image and the image signal corresponding thereto within the reflected image.

Still further, the third fluorescent image obtaining apparatus according to the present invention can also be provided with a display means for displaying a target-subject image based on the image signal read out by the readout means, and the display means can display a target-subject image based on the aforementioned image signals of a predetermined valid range of the fluorescent image and the reflected image, which have been subjected to image processes by the image processing means.

In addition, the third fluorescent image obtaining apparatus according to the present invention can also be provided with a display magnification rate control means for controlling the display magnification rate so that the target-subject image based on the image signal of the predetermined valid range is displayed at a predetermined size.

Additionally, the readout means can be a means for reading out only the image signals of a predetermined valid range of the fluorescent image and the reflected image.

The fourth fluorescent image obtaining apparatus according to the present invention comprises: an illuminating means for guiding an excitation light, a reference-light, and an illuminating-light to a measurement area and illuminating the measurement area with the excitation light, the reference-light, and the illuminating-light; an image obtaining means for obtaining a fluorescent image based on the fluorescent light emitted from the measurement area upon the illumination thereof by the excitation light and which has been passed through an imaging optical system, a reflectance image based on the reflected-light reflected from the measurement area upon the illuminating thereof by the illuminating-light and which has been passed through an imaging optical system, and a reflected image based on the reflected-light reflected from the measurement area upon the illuminating thereof by the reference-light and which has been passed through an imaging optical system; and a readout means for reading out an image signal based on the fluorescent image, an image signal based on the reflectance image, and an image signal based on the reflected image obtained by the image obtaining means; further provided with a statistical quantity computing means for computing a statistical quantity based on the image signal of a predetermined region of the fluorescent image or the reflected image obtained by the image obtaining means; wherein the image obtaining means is provided with a magnification control means for determining the size of the fluorescent image, the reflected image, and the reflectance image by controlling, based on the statistical quantity, the magnification rate of the imaging optical system.

Further, the fourth fluorescent image obtaining apparatus according to the present invention can also be provided with an image processing means for subjecting the image signal read out by the readout means to a predetermined image process, and the image processing means can perform image processes on the image signal of a predetermined valid range of the predetermined region within a fluorescent image and the respective image signals corresponding thereto within the reflected image and the reflectance image.

Still further, the fourth fluorescent image obtaining apparatus according to the present invention can also be provided with a display means for displaying a target-subject image based on the image signal read out by the readout means, and the display means can display a target-subject image based on the aforementioned image signals of a predetermined valid range of the fluorescent image, the reflected image, and the reflectance image and which have been subjected to image processes by the image processing means.

In addition, the fourth fluorescent image obtaining apparatus according to the present invention can also be provided with a display magnification rate control means for controlling the display magnification rate so that the target-subject image based on the image signal of the predetermined valid region is displayed at a predetermined size.

Additionally, the readout means can be a means for reading out only the image signals of a predetermined valid range of the fluorescent image, the reflected image, and the reflectance image.

Here, according to the first, second, third, and fourth embodiments of the fluorescent image obtaining apparatus of the present invention, the referents of the expression "controlling, based on the statistical quantity, the magnification rate of the imaging optical system" include: for a case in which, for example, the statistical quantity of the image signal of the predetermined region of a fluorescent image is less than a desired threshold value, that is, when the size of the image signal of the fluorescent image is not a sufficient size, the magnification rate is controlled so that the size of the fluorescent image is reduced by the imaging optical system; for a case in which the statistical quantity is greater than a desired threshold value, that is, when the size of the image signal of the fluorescent image is large, the magnification rate is controlled so that the size of the fluorescent image is enlarged by the imaging optical system; and for a case in which the statistical quantity is substantially equal to a desired value, that is, when the size of the image signal of the fluorescent image is an appropriate size, the magnification rate is controlled so that the size of the fluorescent image is unchanged, that is focused at a 1:1 size ratio by the imaging optical system. Alternatively, a plurality of threshold values and magnification rates corresponding thereto can be set, and the magnification rate can be changed in a stepped manner. Note that the referent of "the size of the fluorescent image" is the size of the fluorescent image focused on the obtaining element.

Further, the referent of "a statistical quantity based on the image signal" is, for example, the image intensity of a fluorescent image or a reflected image (i.e., the image signal itself), or the statistical quantity computed from the Y signal converted at the time of display (the Y of the YIQ of an NTSC signal, the Y of a YCbCr, etc.), etc. Further, for cases such as those in which brightness data is assigned to the image signal of a reflected image, the aforementioned statistical quantity can be computed from this brightness data. In short, so far as the statistical quantity is computed from an image signal or data based on the image signal of a fluorescent image or a reflected image, any statistical quantity will do.

Still further, according to the second fluorescent image obtaining apparatus of the present invention, the size of the reflectance image can be controlled corresponding to the size of the fluorescent image: for example, for cases in which the imaging optical system reduces or leaves the size of the fluorescent image unchanged as described above, the size of the reflectance image is unchanged; for cases in which the imaging optical system enlarges the fluorescent image, the reflectance image can also be enlarged.

Still further, according to the third fluorescent image obtaining apparatus of the present invention, the size of the reflected image can be controlled corresponding to the size of the fluorescent image: for example, for cases in which the imaging optical system reduces the size of the fluorescent image, the size of the reflected image can also be reduced; for cases in which the magnification rate of the fluorescent image is unchanged, the magnification rate of the reflected image can also be left unchanged; and for cases in which the size of the fluorescent image is enlarged, the size of the reflected image can also be enlarged.

In addition, according to the fourth fluorescent image obtaining apparatus of the present invention, the size of the reflectance image and the size of the reflected image can be controlled corresponding to the size of the fluorescent image: for example, for cases in which the imaging optical system reduces the size of the fluorescent image, the size of the reflectance image can be left unchanged, and the size of the reflected image can also be reduced; for cases in which the size of the fluorescent image is left unchanged, the size of the reflectance image and the size of the reflected image can be left unchanged; and for cases in which the size of the fluorescent image is enlarged, the size of the reflectance image and the size of the reflected image can be enlarged.

Additionally, according to the first and second fluorescent image obtaining apparatuses of the present invention, the predetermined region of the fluorescent image can be the entire said image, and the statistical quantity computing means can compute the statistical quantity of the image signal of the entire said image.

Further, according to the third or fourth fluorescent image obtaining apparatuses of the present invention, the predetermined region can be the entirety of either the fluorescent image or the reflected image, and the statistical quantity computing means can compute the statistical quantity of the image signal of the entirety of either of said images.

Still further, according to the first or second fluorescent image obtaining apparatus of the present invention, the predetermined region can be the region of interest of the fluorescent image, and the statistical quantity computing means can compute the statistical quantity of the image signal of said region of interest of said image.

In addition, according to the third or fourth fluorescent image obtaining apparatus of the present invention, the predetermined region can be the region of interest of the fluorescent image or the reflected image, and the statistical quantity computing means can compute the statistical quantity of the image signal of said region of interest of either of said images.

Here, the referent of the term "region of interest" is, for example, an area of particularly high interest when performing a diagnostic reading of the image.

Additionally, the referent of "predetermined valid range" is, for example, the range within the range in which the actual object of observation is focused on the obtaining element, desired to be displayed as an image when performing a diagnostic reading.

Further, according to the third or fourth fluorescent image obtaining apparatus of the present invention, the statistical computing means can be a means for performing a weighted computation on a predetermined range of a predetermined region corresponding to the degree of interest thereof, and computing the statistical quantity of the computed image signal obtained thereby.

Here, the referent of "performing a weighted computation on a predetermined range of a predetermined region corresponding to the degree of interest thereof" is, for example, the multiplying of the image signal having the highest degree of interest within a predetermined region by a factor of 1, the multiplying of the image signal having a high degree of interest by a factor of 0.5, and the multiplying of the remaining image signal by a factor of 0.1 to weight the image signal according to the respective degree of interest thereof.

Further, according to the first, second, third, and fourth embodiments of the fluorescent image obtaining apparatus of the present invention, the statistical quantity of the image signal consists of at least one of the following: the maximum value, the minimum value, the average value, the combination of the maximum value and the standard deviation, the combination of the minimum value and the standard deviation, and the combination of the mean value and the standard deviation. When either any of said maximum value, minimum value, or average value of the statistical quantity is small, the magnification rate is caused to be small; when either of said values is large, the magnification rate is caused to be large.

Still further, according to the first, second, third, and fourth embodiments of the fluorescent image obtaining apparatus of the present invention, the readout means is capable of controlling, corresponding to the predetermined valid region, the readout frequency.

Here, the referent of "controlling, corresponding to the predetermined valid region, the readout frequency" is, for a case in which the image obtained by the CCD element is read out as an image signal by the readout means, for example, the readout is performed in order of the horizontal/vertical transmission signal based on a standard clock signal by the readout means; however, because the number of pixels to be read out increases in proportion to an expansion of the size of the predetermined valid range, the readout frequency becomes higher. Accordingly, the readout frequency is determined according to the size of the predetermined valid range, and the readout means reads out the image signal according to the horizontal/vertical transmission order thereof.

Further, according to the first, second, third, and fourth embodiments of the fluorescent image obtaining apparatus of the present invention, a bit shifting means can be provided for shifting the bits so that if the pixel data based on the image signal is represented by data constituted of 9 bits or more, said data is expressed by the lower 8 bits thereof, and the statistical quantity computing means can be a means for computing the statistical quantity based on the bit-shifted data.

Still further, according to the first, second, third, and fourth embodiments of the fluorescent image obtaining apparatus of the present invention, a portion or the entirety of the illuminating means, the image obtaining means, and the readout means can be provided in the form of an endoscope provided with an insertion portion to be inserted into a body of a patient.

In addition, the first, second, third, and fourth embodiments of the fluorescent image obtaining apparatus of the present invention can be of a configuration wherein: a portion or the entirety of the illuminating means, the image obtaining means, and the readout means can be disposed within the insertion portion, and the portions of the illuminating means, the image obtaining means, and the readout means other than those portions disposed within the insertion portion can be disposed within a processor section; wherein the imaging optical system, of which the magnification rate is controlled by the magnification rate control means, is disposed within the processor section.

Additionally, the first, second, third, and fourth embodiments of the fluorescent image obtaining apparatus of the present invention, can be of a configuration wherein: a portion or the entirety of the illuminating means, the image obtaining means, and the readout means can be disposed within the insertion portion, and the portions of the illuminating means, the image obtaining means, and the readout means other than those portions disposed within the insertion portion can be disposed within a processor section; wherein the imaging optical system, of which the magnification rate is controlled by the magnification rate control means, is disposed within the insertion portion.

Further, according to the first, second, third, and fourth embodiments of the fluorescent image obtaining apparatus of the present invention, the excitation light source can be a GaN semiconductor laser, and the excitation light can be of a wavelength within the 400–420 nm wavelength range.

According to the first fluorescent image obtaining apparatus of the present invention, the statistical quantity computing means computes the statistical quantity of the image signal of a predetermined region of a fluorescent image obtained by the image obtaining means, and because the magnification rate control means controls, based on the computed statistical quantity, the magnification rate of the imaging optical system so as to determine the size of the fluorescent image, even for cases in which the intensity of the fluorescent image is weak, that is, even when the size of the image signal of the fluorescent image is less than a predetermined value, by the controlling, based on the statistical quantity, of the magnification rate of the imaging optical system so that the fluorescent image is reduced to an appropriate size, the intensity of only the fluorescent image can be amplified, whereby the S/N ratio of the fluorescent image can be improved.

According to the second fluorescent image obtaining apparatus of the present invention, the statistical quantity computing means computes the statistical quantity of the image signal of a predetermined region of a fluorescent image obtained by the image obtaining means, and because the magnification rate control means controls, based on the computed statistical quantity, the magnification rate of the imaging optical system so as to determine the size of the fluorescent image and the reflectance image, in addition to the effects obtained according to the first embodiment described above, the size of the reflectance image can be caused to correspond to the size of the fluorescent image.

According to the third fluorescent image obtaining apparatus of the present invention, the statistical quantity computing means computes the statistical quantity of the image signal of a predetermined region of a fluorescent image or a reflected image obtained by the image obtaining means, and because the magnification rate control means controls, based on the computed statistical quantity, the magnification rate of the imaging optical system so as to determine the size of the fluorescent image and the reflected image, in addition to the effects obtained according to the first embodiment described above, the size of the reflected image can be caused to correspond to the size of the fluorescent image, and even for cases in which the image process is performed utilizing the fluorescent image and the reflected image, adequate interimage image processing can be carried out. Further, for cases in which the statistical quantity computing means computes the statistical quantity of the image signal of a predetermined region of a reflected image, the magnification rate can be controlled so as to be a magnification rate more accurately reflecting the distance between the image obtaining means and the measurement area.

According to the fourth fluorescent image obtaining apparatus of the present invention, the statistical quantity computing means computes the statistical quantity of the image signal of a predetermined region of a fluorescent image or a reflected image obtained by the image obtaining means, and because the magnification rate control means controls, based on the computed statistical quantity, the magnification rate of the imaging optical system so as to determine the size of the fluorescent image, the reflected image, and the reflectance image, the same effects obtained according to the first through the third embodiment described above can be obtained.

Further, according to the first, second, third, and fourth embodiments of the fluorescent image obtaining apparatus of the present invention, for cases in which the image processing means is a means for performing image processes on the image signal of a predetermined valid range of a predetermined region of an image, the image processing time can be shortened.

Still further, according to the first, second, third, and fourth embodiments of the fluorescent image obtaining apparatus of the present invention, for cases in which the display means is a means for displaying a target-subject image based on the image signal of a predetermined valid range of a predetermined region that has been subjected to an image process by the image processing means, only a particular region having a high degree of interest can be displayed as a target-subject image.

In addition, according to the first, second, third, and fourth embodiments of the fluorescent image obtaining apparatus of the present invention, for cases in which the display magnification rate of a target-subject image based on a predetermined valid region is controlled so as that the target-subject image is displayed at a predetermined size, even if the target-subject is reduced by the imaging optical system, the visual recognition thereof can be ensured for by applying an enlargement display thereto.

Additionally, according to the first, second, third, and fourth embodiments of the fluorescent image obtaining apparatus of the present invention, for cases in which the readout means is a means for reading out only the image signal of a predetermined valid range of a predetermined region of an image, the readout time can be shortened.

Further, according to the first and second embodiments of the fluorescent image obtaining apparatus of the present invention, for cases in which a predetermined region is taken as the entire fluorescent image, and the statistical quantity computing means computes the statistical quantity of the image signals of the entire fluorescent image, a statistical quantity more appropriately reflecting the entire fluorescent image can be computed.

Additionally, according to the third and fourth embodiments of the fluorescent image obtaining apparatus of the present invention, for cases in which a predetermined region is taken as the entire fluorescent image or the entire reflected image, and the statistical quantity computing means computes the statistical quantity of the image signals of the entire fluorescent image or the reflected image, a statistical quantity more appropriately reflecting the entire fluorescent image or reflected image can be computed; in particular, for cases in which the statistical quantity of the entire image signal of the reflected image is computed, a statistical quantity more accurately reflecting the distance between the image obtaining means and the measurement area can be computed.

Further, according to the first and second embodiments of the fluorescent image obtaining apparatus of the present invention, for cases in which a predetermined region is taken as the region of interest of the fluorescent image, and the statistical quantity computing means computes the statistical quantity of the image signal of the region of interest, a statistical quantity more appropriate to the region of interest can be computed.

Still further, according to the third and fourth embodiments of the fluorescent image obtaining apparatus of the present invention, for cases in which a predetermined region is taken as the region of interest of the fluorescent image or the reflected image, and the statistical quantity computing means computes the statistical quantity of the image signal of the region of interest, a statistical quantity more appropriate to the region of interest can be computed; in particular, for cases in which the statistical quantity of the entire image signal of the reflected image is computed, a statistical quantity more accurately reflecting the distance between the image obtaining means and the measurement area can be computed.

Further, according to the first, second, third and fourth embodiments of the fluorescent image obtaining apparatus of the present invention, for cases in which the statistical quantity computing means computes the statistical quantity of the image signals within a predetermined region within a predetermined range, weighted according to the level of interest thereof, a statistical quantity that more appropriately reflects a region with a high level of interest can be computed for a fluorescent image or a reflected image.

In addition, according to the first, second, third, and fourth embodiments of the fluorescent image obtaining apparatus of the present invention, for cases in which the statistical quantity of the image signal consists of at least one of the following: the maximum value, the minimum value, the mean value, the combination of the maximum value and the standard deviation, the combination of the minimum value and the standard deviation, the combination of the mean value and the standard deviation, and the magnification rate is caused to be small when any of said maximum value, minimum value, or average value of the statistical quantity is small, or the magnification rate is caused to be large when any of said values is large, the statistical quantity can be computed with ease, and the magnification rate can be controlled so that it reflects the statistical quantity.

Additionally, according to the first, second, third, and fourth embodiments of the fluorescent image obtaining apparatus of the present invention, for cases in which the readout means controls, corresponding to the predetermined valid region, the readout frequency, because the readout frequency can be controlled so as to be the minimum required readout frequency, the readout noise occurring in conjunction with the readout processing can be reduced, and the S/N ratio of the fluorescent image, the reflected image, and the reflectance image can be improved.

Further, according to the first, second, third, and fourth embodiments of the fluorescent image obtaining apparatus of the present invention, in the case that a bit shifting means is provided for shifting the bits so that, if the pixel data based on the image signal is represented by data constituted of 9 bits or more, said data is expressed by the lower 8 bits thereof, and the statistical quantity computing means is a means for computing the statistical quantity based on the bit-shifted data, a common 8-bit calculator can be employed and the processing speed can be increased.

Still further, according to the first, second, third, and fourth embodiments of the fluorescent image obtaining apparatus of the present invention, for cases in which a portion or the entirety of the illuminating means, the image obtaining means, and the readout means is provided in the form of an endoscope provided with an insertion portion to be inserted into a body cavity of a patient, the fluorescent image obtaining apparatus according to the present invention can be effectively employed as an endoscope apparatus.

In addition, for cases in which the fluorescent image obtaining apparatus according to the first, second, third, and fourth embodiments of the present invention is of a configuration wherein: a portion or the entirety of the illuminating means, the image obtaining means, and the readout means is disposed within the insertion portion; the portions of the illuminating means, the image obtaining means, and the readout means other than those portions disposed within the insertion portion can be disposed within a processor section; and the imaging optical system, of which the magnification rate is controlled by the magnification rate control means, is disposed within the processor section; the configuration of the insertion portion can be simplified, and an increase in performance attained due to a reduction to the weight of the insertion portion.

Additionally, for cases in which the fluorescent image obtaining apparatus according to the first, second, third, and fourth embodiments of the present invention is of a configuration wherein: a portion or the entirety of the illuminating means, the image obtaining means, and the readout means is disposed within the insertion portion; the portions of the illuminating means, the image obtaining means, and the readout means other than those portions disposed within the insertion portion can be disposed within a processor section; and the imaging optical system, of which the magnification rate is controlled by the magnification rate control means, is disposed within the insertion portion, the size of the apparatus can be made more compact.

Further, according to the first, second, third, and fourth embodiments of the fluorescent image obtaining apparatus of the present invention, for cases in which the excitation light source is a GaN semiconductor laser and the excitation light is of a wavelength within the 400–420 nm wavelength range, fluorescent light can be caused to be more efficiently emitted from a measurement area.

BRIEF DESCRIPTION OF THE DRAWINGS

FIG. 1 is a schematic drawing of a fluorescent endoscope implementing the fluorescent image obtaining apparatus according to the first embodiment of the present invention.

DESCRIPTION OF THE PREFERRED EMBODIMENTS

Figure 2:
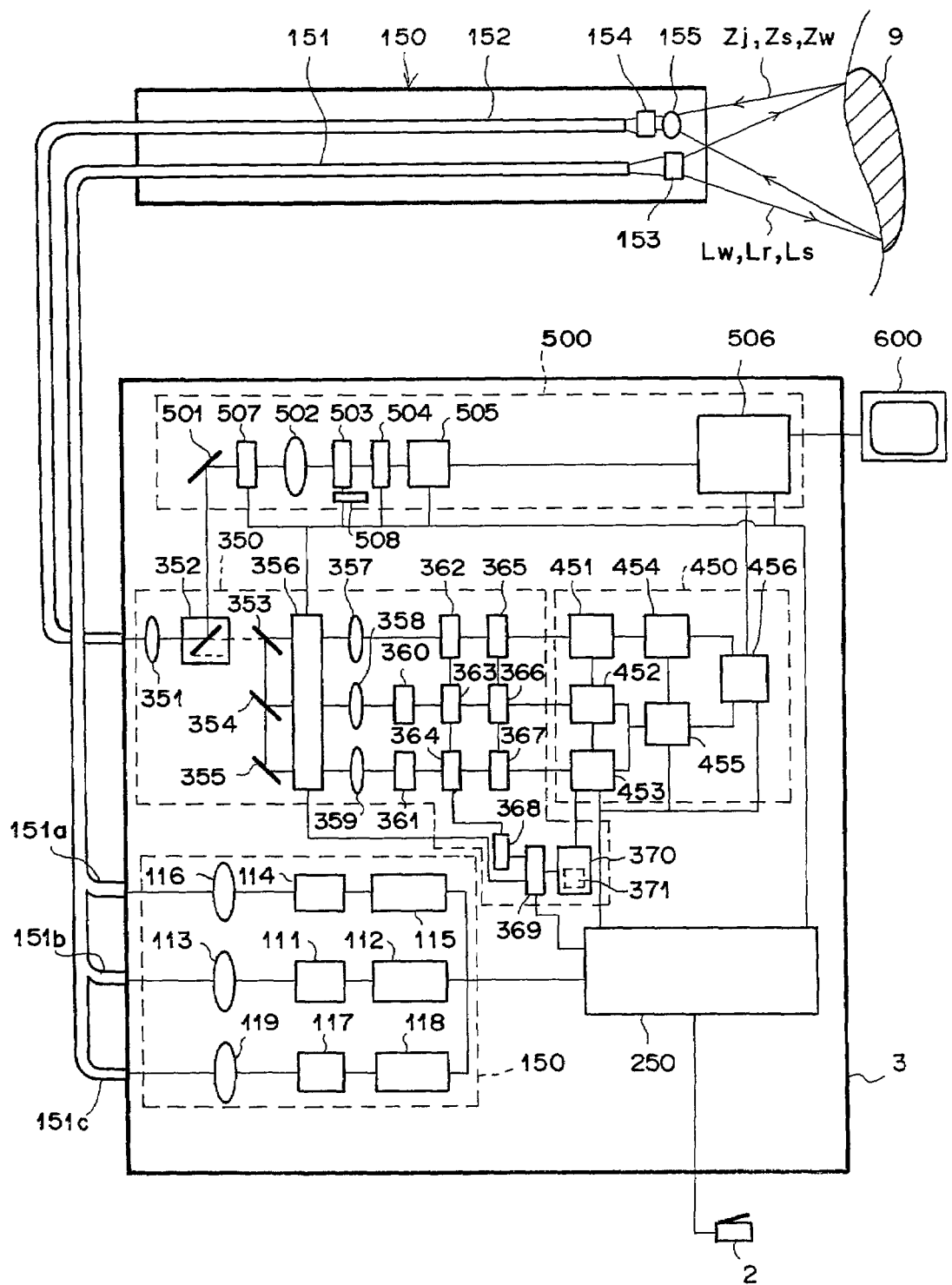
FIG. 2 is a schematic drawing of an endoscope implementing the fluorescent image obtaining apparatus according to the second embodiment of the present invention.

Hereinafter, the preferred embodiments of a fluorescent endoscope implementing the fluorescent image obtaining apparatus according to the present invention will be explained with reference to the attached drawings. FIG. 1 is a schematic drawing of a fluorescent endoscope according to the first embodiment of the present invention.

The fluorescent endoscope according to the first embodiment comprises: an endoscope insertion portion 100 to be inserted into the primary nidus and areas of suspected secondary infection of a patient; an image signal processing portion 1 for processing the data obtained of a living-tissue subject (hereinafter referred to as a target subject) into an image signal; and a monitor 600 for displaying the signal processed by the image signal processing portion 1 as a visible image. The image signal processing portion 1 comprises: an illuminating unit 110 provided with two light sources for emitting a white light Lw for obtaining a reflectance image and an excitation light Lr for obtaining an autofluorescent image, respectively; an image detecting unit 300 for obtaining an autofluorescent image Zj formed of the autofluorescent light emitted from a target subject 9 upon the irradiation thereof by the excitation light Lr, converting said obtained autofluorescent image Zj to a digital value and outputting said digital value as image data; an image computing unit 400 for subjecting the image data of the autofluorescent image outputted from the image detecting unit 300 to computational processes such as distance correction and signal processes, and outputting the resulting signal; a display signal processing unit 500 for converting a reflectance image to a digital value to obtain image data thereof, and converting said image data and the signal outputted from the image computing unit 400 to a video signal and outputting said video signal; and a footswitch 2 for switching between a reflectance image display mode and a composite image display mode.

The endoscope insertion portion 100 is provided with a light guide 101 extending internally to the distal end thereof, and an image fiber 102. An illuminating lens 103 is provided at the distal end portion of the light guide 101, that is, at the distal end of the endoscope insertion portion 100. Further, the image fiber 102 is formed of a composite glass fiber, and an excitation light cutoff filter 104 as well as a focusing lens 105 are provided at the distal end portion thereof. The light guide 101 consists of a bundled white-light guide 101a and excitation-light guide 101b in the form of an integrated cable; the white-light guide 101a and excitation-light guide 101b are connected to the illuminating unit 110. One end of the image fiber 102 is connected to the image detecting unit 300.

The illuminating unit 110 comprises: a GaN semiconductor laser 111 that emits an excitation light Lr for obtaining autofluorescent images and a semiconductor laser power source 112 electrically connected thereto; and a white-light source 114 that emits a white light Lw for obtaining reflectance images and a white-light source power source 115 electrically connected thereto.

The image fiber 102 is connected to the image detecting unit 300. Said image detection unit 300 comprises: a collimator lens 301 that focuses an autofluorescent image or a reflectance image conveyed thereto via the image fiber 102; a movable mirror 302 that totally reflects in a perpendicular direction a reflectance image transmitted by the collimator lens 301, and moves into the position indicated by the broken line and allows a fluorescent image transmitted by the collimator lens 301 to pass; a half mirror 303 that transmits 50% of the light (having a wavelength of 750 nm or shorter) of an autofluorescent image transmitted by the collimator lens 301 and reflects perpendicularly 50% of said light; a fluorescent image mirror 304 that perpendicularly reflects the light of the autofluorescent image reflected by the half mirror 303; an imaging optical system 305 that controls the magnification rate, by use of the magnification rate control means 316 described below, of the autofluorescent image and the fluorescent image transmitted by the half mirror 303 and the autofluorescent image reflected by the fluorescent image mirror 304 so that the magnification rate thereof is such that each said image is enlarged, reduced, or focused at a 1:1 magnification rate; a wide-band fluorescent image lens 306 and a narrow-band fluorescent image lens 307 that focus an autofluorescent image transmitted by the imaging optical system at a predetermined magnification rate; awide-band band pass filter 308 that selects the light having a wavelength within the 430–730 nm wavelength range from the autofluorescent image transmitted by the wide-band fluorescent image lens 306; a wide-band fluorescent image high-sensitivity obtaining element 310 that obtains as an autofluorescent image the autofluorescent-light transmitted by the wide-band band pass filter 308; a narrow-band band pass filter 309 that selects the light having a wavelength within the 430–530 nm wavelength range from the autofluorescent image transmitted by the narrow-band fluorescent image lens 307; a narrow-band fluorescent image high-sensitivity obtaining element 311 that obtains as an autofluorescent image the autofluorescent-light transmitted by the narrow-band band pass filter 309; a readout means 314 that controls, based on a control signal from the magnification rate control means described below, the drive range occurring in the wide-band fluorescent image high-sensitivity obtaining element 310 and the narrow-band fluorescent image high-sensitivity obtaining element 311 and reads out the image signal of said drive range; an AD converter 312 that converts the image signal outputted by the wide-band fluorescent image high-sensitivity obtaining element 310, based on a control signal from the readout means 314, to a digital value, and outputs said digital value as an image signal; an AD converter 313 that converts the image signal outputted by the narrow-band fluorescent image high-sensitivity obtaining element 311, based on a control signal from the readout means 314, to a digital value, and outputs said digital value as an image signal; a statistical quantity computing means 315 that computes a statistical quantity based on the image data outputted from the AD converter 312 and stored in a wide-band fluorescent image memory 401, which is described below, and the image data outputted from the AD converter 313 and stored in a narrow-band fluorescent image memory 402, which is described below; and a magnification rate control means 316 that determines, based on the statistical quantity outputted from the statistical quantity computing means 315, the magnification rate of the imaging optical system 305 and the magnification rate of the reflectance image imaging optical system 507 described below, and outputs a magnification rate control signal so that the magnification rate of the imaging optical system 305 and the magnification rate of the reflectance image imaging optical system 507 is caused to become said determined magnification rate, and also determines, based on said magnification rate, the drive range occurring in the wide-band fluorescent image high-sensitivity obtaining element 310, the narrow-band fluorescent image high-sensitivity obtaining element 311, and the reflectance image obtaining element 503, which is described below, and outputs a control signal to the readout means 314 and the readout means 508, which is described below, so that the image signal occurring in said determined range is read out. Note that the statistical quantity computing means 315 is provided with a bit shifting means 317 for shifting the number of bits of the image data to 8 bits or less when the statistical quantities of said data are computed.

The image computing unit 400 comprises: a wide-band fluorescent image memory 401 that stores the wide-band autofluorescent image data outputted from the AD converter 312; a narrow-band fluorescent image memory 402 that stores the narrow-band autofluorescent image data outputted from the AD converter 313; and a color image forming means 403 that performs computational processing according to the comparative ratio between the corresponding pixel values of the image data of the wide-band autofluorescent image stored in the wide-band fluorescent image memory 401 and the narrow-band autofluorescent image stored in the wide-band fluorescent image memory 402 to obtain a computed value for each pixel, and assigns a color data to each pixel based on the size of said obtained value to form a color image, which is then outputted therefrom.

The display signal processing unit 500 comprises: a reflectance image mirror 501 that perpendicularly reflects a reflectance image reflected by the movable mirror 302; a reflectance image imaging optical system 507 that causes the magnification rate of the reflectance image reflected by the reflectance image mirror 501 to be an enlargement magnification rate or a 1:1 magnification rate, and transmits said reflectance image; a reflectance image focusing lens 502 that focuses the reflectance image that has been caused to have an enlargement magnification rate or a 1:1 magnification rate by the image imaging optical system 507; a reflectance image obtaining element 503 that obtains the reflectance image focused by the reflectance image focusing lens 502; a readout means 508 that controls, based on a control signal outputted by the magnification rate control means 316, the drive range occurring in the reflectance image obtaining element 503 and reading out the image signal of said drive range; an AD converter 504 that converts the image signal outputted by the reflectance image obtaining element 503, based on a control signal from the readout means 508, to a digital value, and outputs said digital value as an image signal; a reflectance image memory 505 that stores said digitized image signal; and a video signal processing circuit 506 that converts the image signal outputted by the reflectance image memory 505 and the color image signal outputted from the image forming means 403 to video signals and outputs said video signals. The monitor 600 is a means that switches between the displaying of the reflectance image and the color image.

Next, the operation of the fluorescent endoscope according to the current embodiment will be explained. First, the operation occurring when a color image is to be displayed using an autofluorescent image formed of two different wavelength bands will be explained.

Based on a signal outputted from a control computer 200, the semiconductor-laser power source 112 is activated and the excitation light Lr is emitted from the GaN semiconductor laser 111. The excitation light Lr emitted by the GaN semiconductor laser 111 is transmitted by an excitation light focusing lens 113 and enters the light guide 101b, and after being guided to the distal end of the endoscope insertion portion 100, said excitation light Lr is projected from the illuminating lens 103 onto the target subject 9. The autofluorescent image formed of the autofluorescent light emitted from the target subject 9 upon the irradiation thereof by the excitation light Lr is focused by the focusing lens 105, transmitted by the excitation light cutoff filter 104, enters the distal end of the image fiber 102, and enters the collimator lens 301 via the image fiber 102. The excitation light cutoff filter 104 is a long-pass filter for passing all light having a wave length of 420 nm or longer. Because the wavelength of the excitation light is 410 nm, the excitation light reflected from the target subject 9 is cutoff by this excitation light cutoff filter 104. The autofluorescent image transmitted by the collimator lens 301 is transmitted at a transmittance rate of 50% and reflected at a reflectance rate of 50% by the half mirror 303. The autofluorescent image perpendicularly reflected by the half mirror 303 is perpendicularly reflected by the fluorescent image mirror 304. The autofluorescent image transmitted by the half mirror 303 and the autofluorescent image reflected by the fluorescent image mirror 304 enter the imaging optical system 305 together. At this time, the autofluorescent image that enters the imaging optical system 305 first is transmitted thereby at a 1:1 magnification rate. The autofluorescent image that has been transmitted by the imaging optical system 305 at a 1:1 magnification rate is focused by the wide-band fluorescent image lens 306, and the autofluorescent image transmitted by the wide-band fluorescent image lens 306 is transmitted by the wide-band band pass filter 308, and is obtained by the wide-band fluorescent image high-sensitivity obtaining element 310. The autofluorescent image reflected by the fluorescent image mirror 304 is focused by the narrow-band fluorescent image lens 307, and the autofluorescent image transmitted by the narrow-band fluorescent image lens 307 is transmitted by the narrow-band band pass filter 309, and is obtained by the narrow-band fluorescent image high-sensitivity obtaining element 311.

The autofluorescent image is obtained by the wide-band fluorescent image high-sensitivity obtaining element 310 and the narrow-band fluorescent image high-sensitivity obtaining element 311 and converted to image signals that are electrical signals, and each is read out, based on a control signal from the readout means 314, as an image signal, respectively. Then, the image signal read out from the wide-band fluorescent image high-sensitivity obtaining element 310 is inputted to the AD converter 312 and digitized thereby, after which said digitized signal is stored in the wide-band fluorescent image memory 401. The image signal read out from the narrow-band fluorescent image high-sensitivity obtaining element 311 is inputted to the AD converter 313 and digitized thereby, after which said digitized signal is stored in the narrow-band fluorescent image memory 402.

Figure 3:
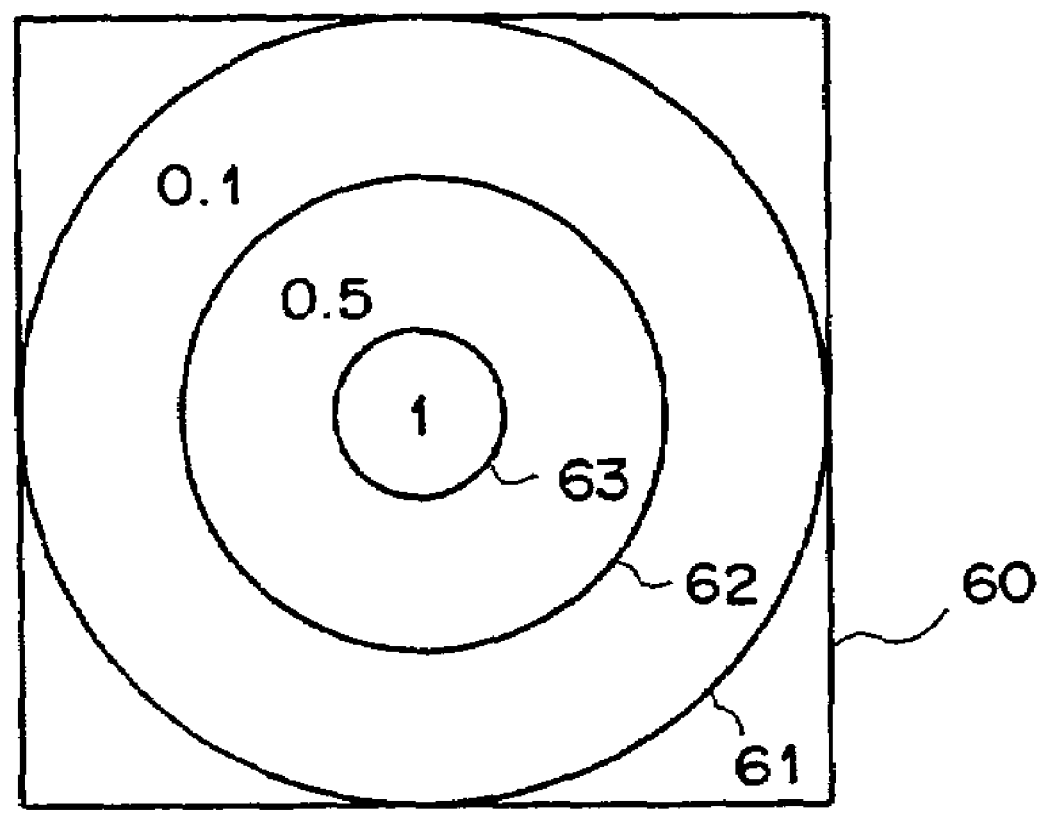
FIG. 3 is a drawing illustrating the concept of weighted processing.

Here, after the initially obtained autofluorescent image has been stored in the wide-band fluorescent image memory 401 and the narrow-band fluorescent image memory 402, the statistical quantity of the image data of a region of interest from among the image data is outputted to the statistical quantity computing means. In a case, for example, in which the image data stored in the wide-band fluorescent image memory 401 and the narrow-band fluorescent image memory 402 is represented by the region 60 shown in FIG. 3, the image data of the region of interest 61 within the region 60 is outputted. The region of interest can be a region that has been set in advance, or a region that is set by use of a predetermined setting means (not shown). Further, after the image data of the region of interest 61 outputted to the statistical quantity computing means 315 has been bit shifted to data containing 8 bits or less by the bit shifting means 317, the statistical quantity computing means 315 performs weighted computational processing on said bit-shifted data, which weights said bit-shifted data corresponding to the degree of interest thereof. For example, if a region 63 within the region of interest 61 is taken as the region having the highest degree of interest, the image signal of the region 63 is multiplied by a multiplier of 1; next, the region having a high degree of interest other than region 63 is designated as the region 62, and the image data of this region 62 is multiplied by a multiplier of 0.5; further, the region having a high degree of interest other than regions 62 and 63 is designated as the region 61, and the image data of this region 61 is multiplied by a multiplier of 0.1. Then, the mean value of all the weighted image data of the region 61 is obtained. This average value is then outputted to the magnification rate control means 316, and the magnification rate control means 316 determines, according to said mean value, the magnification rates of the autofluorescent image and the reflectance image; the magnification rate control means 316 then outputs a control signal to the imaging optical system 305 and the reflectance image imaging optical system 507 so as to cause the magnification rate to become said determined magnification rate. The magnification rate setting means 316 is a means in which an appropriate magnification rate for the imaging optical system 305 and the reflectance image imaging optical system 507 has been set corresponding to the average value outputted thereto from the statistical quantity computing means 315. In a case, for example, in which the average value is smaller than a predetermined value, that is, when the size of the image signal of the autofluorescent image is not of a sufficient size, this set magnification rate is a magnification rate that causes the size of the autofluorescent image to be reduced by the imaging optical system 305; or, for a case in which the average value is larger than the predetermined value, that is, when the size of the image signal of the autofluorescent image is large, this set magnification rate is a magnification rate that causes the size of the autofluorescent image to be enlarged by the imaging optical system 305; or for a case in which the average value is substantially equal to the predetermined value, that is, when the size of the image signal of the autofluorescent image is an appropriate size, this set magnification rate is a magnification rate that causes the size of the autofluorescent image to be focused at a 1:1 magnification rate by the imaging optical system 305.

Then, the next autofluorescent image passes through the imaging optical system 305, of which the magnification rate has been caused to be an appropriate magnification rate based on the magnification rate control signal from the magnification rate control means 316, and is obtained. Further, the magnification rate control means outputs the drive range corresponding to the valid region occurring within the region of interest to the readout means 314, and the readout means 314 reads out the image data, corresponding to the drive range of said valid region, of the narrow-band fluorescent image high-sensitivity obtaining element 311 and the wide-band fluorescent image high-sensitivity obtaining element 310. This drive range of the valid region is the region that is desired to be displayed as an image, and can be a preset region or a region set by use of a predetermined input means (not shown). Further, for cases in which the narrow-band fluorescent image high-sensitivity obtaining element 311 and the wide-band fluorescent image high-sensitivity obtaining element 310 are CCDs, the readout means 314 carries out the readout by the concurrent horizontal/vertical signals thereof as well as a standard clock signal, and the control of the drive range of the valid region is carried out by the change of the frequency of the concurrent horizontal/vertical signals thereof as well as the standard clock signal. For cases in which an autofluorescent image that has been reduced by the imaging optical system 305 is obtained, because the readout frequency becomes lower, the readout noise of the CCD can be controlled thereby.

The read out image data, which corresponds to the drive range of the valid region, is stored in the narrow-band fluorescent image memory 318 and the wide-band fluorescent image memory 319.

Then, the image forming means 403 subjects the narrow-band fluorescent image of the valid region stored in the narrow-band fluorescent image memory 318 and the wide-band fluorescent image of the valid region stored in the wide-band fluorescent image memory 319 to computational processing according to the comparative ratio between the corresponding pixel values thereof to obtain a computed value for each pixel, assigns color data to each computed value, and forms and outputs an image signal having color data. The color image formed by the image forming means 403 is DA converted by the video signal processing circuit 506, and then inputted to the monitor 600 and displayed thereon as a color image of the valid region. It becomes possible to determine whether a tissue is a diseased tissue or a normal tissue based on the difference in the colors appearing in this color image.

Next the operation occurring when a reflectance image is to be displayed will be explained. First, based on a signal outputted from a control computer 200, the white-light power source 115 is activated and the white light Lw is emitted from the white-light-source 114. The white light Lw emitted by the white-light source 114 is transmitted by a white-light focusing lens 116 and enters the white-light guide 101*a*, and after being guided to the distal end of the endoscope insertion portion 100, said white light Lw is projected from the illuminating lens 103 onto the target subject 9. The reflectance image formed of the white light Lw reflected from the target subject 9 upon the irradiation thereof by the white light Lw is focused by the focusing lens 105, transmitted by the excitation light cutoff filter 104 and enters the distal end of the image fiber 102; said reflected white light Lw enters the collimator lens 301 via the image fiber 102. The reflected light transmitted by the collimator lens 301 is reflected by the movable mirror 302 and the reflectance image mirror 501, and enters the reflectance image imaging optical system 507. At this time, the magnification rate of the reflectance image imaging optical system 507 is controlled, based on a magnification rate control signal outputted from the magnification rate control means 316. The magnification rate of the reflectance image imaging optical system 507 at this time is, in a case, for example, in which the magnification rate of the imaging optical system 305 has been controlled so as to enlarge the autofluorescent image, controlled so as to have the same magnification rate as the imaging optical system 305 and the reflectance image is enlarged. Further, for cases in which the magnification rate of the imaging optical system 305 has been controlled so as to reduce or focus the autofluorescent image at a 1:1 magnification rate, the magnification rate of the reflectance image imaging optical system 507 is controlled so that the magnification rate thereof is 1:1, and the reflectance image is transmitted. A reflectance image that has been focused at an appropriate magnification rate by the reflectance image imaging optical system 507 enters the reflectance image focusing lens 502. The reflectance image transmitted by the reflectance image focusing lens 502 is focused onto the reflectance image obtaining element 503. Here, under the control of the readout means 508, the image data of the reflectance image corresponding to the valid region of the aforementioned autofluorescent image is read out at the reflectance image obtaining element 503. The image data of the valid region, which is outputted from the reflectance image obtaining element 503 is inputted to the AD converter 504 and digitized thereby, after which said digitized signal is stored in the reflectance image memory 505. The image signal of the valid region, which has been stored by said reflectance image memory 505, is DA converted by the video signal processing circuit 506, and then inputted to the monitor 600 and displayed thereon as a visible image. Note that the signal processing occurring at the video signal processing circuit 560 during illumination can be a sequential illumination process or a simultaneous illumination process.

The series of operations relating to the displaying of a color image and the displaying of a reflectance image are controlled by the control computer 200. Further, the operation for switching between the color image display mode and the reflectance image display mode is performed by depressing the footswitch 2.

According to the fluorescent endoscope apparatus implementing the fluorescent image obtaining apparatus of the present invention: the statistical quantity computing means 315 computes the statistical quantity of the image signal of a predetermined region of a fluorescent image; and because the magnification rate control means 316 controls, based on the computed statistical quantity, the magnification rate of the imaging optical system 305 so as to determine the size of the fluorescent image, even for cases in which the intensity of the fluorescent image is weak, that is, even when the size of the image signal of the fluorescent image is less than a predetermined value, by the controlling, based on the statistical quantity, of the magnification rate of the imaging optical system so that the fluorescent image is reduced to an appropriate size, the intensity of only the fluorescent image can be amplified, whereby the S/N ratio of the fluorescent image can be improved.

Further, because the image computing means 400 is a means for performing image processing on the image signal of a predetermined valid range within a predetermined region, the image processing time can be shortened.

Still further, because the monitor 600 is a means for displaying a target-subject image based on the image signal of a predetermined valid range within a predetermined region, which has been subjected to image processes by the image computing unit 400, a target-subject image based only on a region having a particularly high degree of interest can be displayed. Further, at this time, if a configuration wherein the size of the target-subject image displayed on the monitor 600 changes according to the magnification rate controlled by the magnification rate control means 316 is adopted (for example, if the autofluorescent image is reduced by the magnification rate control means 400, the target-subject image is also reduced), the mosaic phenomenon occurring within a target-subject image due to a decrease in the number of pixels constitutive thereof can be reduced.

In addition, because the readout means 314 is a means that only reads out the image signal of a predetermined valid range, the readout processing time can be shortened.

Additionally, because the readout means 314 is a means wherein the readout frequency thereof is controlled according to the predetermined region, the readout frequency can be controlled so as to be the minimum required frequency, whereby the readout noise generated during read out can be controlled, the S/N ratio of the fluorescent image, the reflected image, and the reflectance image can be improved.

Further, because the statistical quantity computing means 315 computes the statistical quantity based on data that has been bit shifted so as to be composed of 8-bits or less, by the bit shifting means 317, an ordinary 8-bit calculator can be employed, whereby the speed with which the image processing is performed can be increased.

Next, a fluorescent endoscope implementing a second embodiment of the fluorescent image obtaining apparatus according to the present invention will be explained. FIG. 2 is a schematic drawing of a fluorescent endoscope according to the second embodiment of the present invention. Note that elements in common with those occurring in the first embodiment described above are likewise labeled, and in so far as it is not particularly required, further explanation thereof has been omitted.

The fluorescent endoscope according to the second embodiment comprises: an endoscope insertion portion 150 to be inserted into the primary nidus and areas of suspected secondary infection of a patient; an image signal processing portion 3 that processes the data obtained of a target subject into an image signal; and a monitor 600 that displays the signal processed by the image signal processing portion 3 as a visible image. The image signal processing portion 3 comprises: an illuminating unit 150 provided with three separate light sources that emit a white light Lw for obtaining a reflectance image, an excitation light Lr for obtaining an autofluorescent image, and a reference light Ls for obtaining a reference image, respectively; an image detecting unit 350 that obtains an autofluorescent image Zj formed of the autofluorescent light emitted from a target subject 9 upon the irradiation thereof by the excitation light Lr, and a reflected image Zs formed of the reflected reference light reflected from the target subject 9 upon the irradiation thereof by the reference light Ls, and converts said obtained autofluorescent image Zj and reflected image Zs to digital values and outputs said digital values as image data; an image computing unit 450 that subjects the image data of the autofluorescent image outputted from the image detecting unit 350 to computational processes such as distance correction and assigns color data to the computed value obtained thereby, as well as assigning brightness data to the reflected image Zs and combining and outputting these two image data; a display signal processing unit 500 that converts a reflectance image to a digital value to obtain image data thereof, and converts said image data and the signal outputted from the image computing unit 450 to a video signal and outputs said video signal; and a footswitch 2 that switches between a reflectance image display mode and a composite image display mode.

The endoscope insertion portion 150 is provided with a light guide 151 extending internally to the distal end thereof, and an image fiber 152. An illuminating lens 153 is provided at the distal end portion of the light guide 151, that is, at the distal end of the endoscope insertion portion 150. Further, the image fiber 152 is formed of a composite glass fiber, and an excitation light cutoff filter 154 as well as a focusing lens 155 are provided at the distal end portion thereof. The light guide 151 consists of a bundled white-light guide 151*a* and excitation-light guide 151*b* in the form of an integrated cable; the white-light guide 151*a* and excitation-light guide 151*b* are connected to the illuminating unit 150. One end of the image fiber 152 is connected to the image detecting unit 350.

The illuminating unit 150 comprises: a GaN semiconductor laser 111 that emits an excitation light Lr for obtaining autofluorescent image s and a semiconductor laser power source 112 electrically connected thereto; a white-light source 114 that emits a white light Lw for obtaining reflectance images and a white-light source power source 115 electrically connected thereto; and a reference light source 117 that emits a reference light Ls for obtaining reflectance images and a reference light source power source 118 electrically connected thereto.

The image fiber 152 is connected to the image detecting unit 350. Said image detection unit 350 comprises: a collimator lens 351 that focuses an autofluorescent image, a reflectance image, and a reflected image conveyed thereto via the image fiber 152; a movable mirror 352 that totally reflects in a perpendicular direction a reflectance image transmitted by the collimator lens 351, and moves into the position indicated by the broken line and allows an autofluorescent image and a reflected image transmitted by the collimator lens 351 to pass; a dichroic mirror 353 that perpendicularly reflects the light (having a wavelength of 750 nm or shorter) of the autofluorescent image transmitted by the collimator lens 351 and transmits the light of the reflected image transmitted by the collimator lens 351; a half image mirror 354 that transmits 50% and reflects 50% of the quantity of the light of the autofluorescent image perpendicularly reflected by the dichroic mirror 353; a narrow-band fluorescent image mirror 355 that perpendicularly reflects the autofluorescent image transmitted by the half mirror 354; an imaging optical system 356 that controls the magnification rate, by use of the magnification rate control means 369 described below, of the reflected image transmitted by the dichroic mirror 353, the autofluorescent image perpendicularly reflected by the half mirror 354, and the autofluorescent image reflected by the narrow-band fluorescent image mirror 35 so that the magnification rate thereof is such that each said image is enlarged, reduced, or focused at a 1:1 magnification rate and transmitted; a wide-band fluorescent image lens 358, a narrow-band fluorescent image lens 359, and a reflected image focusing lens 357 that focus an autofluorescent image and a reflected image transmitted by the imaging optical system 356 at a predetermined magnification rate; a wide-band band pass filter 360 that selects the light having a wavelength within the 430–730 nm wavelength range from the autofluorescent image transmitted by the wide-band fluorescent image lens 358; a wide-band fluorescent image high-sensitivity obtaining element 363 that obtains the autofluorescent image transmitted by the wide-band band pass filter 360; a narrow-band band pass filter 361 that selects the light having a wavelength within the 430–530 nm wavelength range from the autofluorescent image transmitted by the narrow-band fluorescent image lens 359; a narrow-band fluorescent image high-sensitivity obtaining element 364 that obtains the autofluorescent image transmitted by the narrow-band band pass filter 361; a reflected image obtaining element 362 that obtains the reflected image transmitted by the reflected image focusing lens 357; a readout means 368 that controls, based on a control signal from the magnification rate control means 369 described below, the drive range occurring in the wide-band fluorescent image high-sensitivity obtaining element 363, the narrow-band fluorescent image high-sensitivity obtaining element 364, and the reflected image obtaining element 362 and reads out the image signal of said drive range; an AD converter 366 that converts the image signal outputted by the wide-band fluorescent image high-sensitivity obtaining element 363, based on a control signal from the readout means 368, to a digital value, and outputting said digital value as an image signal; an AD converter 367 that converts the image signal outputted by the narrow-band fluorescent image high-sensitivity obtaining element 364, based on a control signal from the readout means 368, to a digital value, and outputs said digital value as an image signal; an AD converter 365 that converts the image signal outputted by the reflected image obtaining element 362, based on a control signal from the readout means 368, to a digital value, and outputs said digital value as an image signal; a statistical quantity computing means 370 that computes a statistical quantity based on the image data outputted from the AD converter 366 and stored in a wide-band fluorescent image memory 452, which is described below, and the image data outputted from the AD converter 367 and stored in a narrow-band fluorescent image memory 453, which is described below; and a magnification rate control means 369 that determines, based on the statistical quantity outputted from the statistical quantity computing means 370, the magnification rate of the imaging optical system 356 and the magnification rate of the reflectance image imaging optical system 507, and outputs a magnification rate control signal so that the magnification rate of the imaging optical system 356 and the magnification rate of the reflectance image imaging optical system 507 is caused to become said determined magnification rate, and also determines, based on said magnification rate, the drive range occurring in the wide-band fluorescent image high-sensitivity obtaining element 363, the narrow-band fluorescent image high-sensitivity obtaining element 364, the reflected image obtaining element 362, and the reflectance image obtaining element 503, and outputs a control signal to the readout means 368 and the readout means 508, so that the image signal occurring in said determined range is read out. Note that the statistical quantity computing means 370 is provided with a bit shifting means 371 for shifting the number of bits of the image data to 8 bits or less when readout of said image data is performed.

The image computing unit 450 comprises: a wide-band fluorescent image memory 452 that stores the wide-band autofluorescent image data outputted from the AD converter 366; a narrow-band fluorescent image memory 453 that stores the narrow-band autofluorescent image data outputted from the AD converter 367; a reflected image memory 451 that stores the reflected image data outputted from the AD converter 365; and a fluorescent image computing means 455 that performs computational processing according to the comparative ratio between the corresponding pixel values of the image data of the wide-band autofluorescent image stored in the wide-band fluorescent image memory 401 and the narrow-band autofluorescent image stored in the wide-band fluorescent image memory 402 to obtain a computed value for each pixel thereof, assigning a color data to each pixel based on the size of said obtained value to form a color image, and outputting said color image; a reflectance image computing means 454 that assigns brightness data to the reflectance image data stored in the reflectance image memory 451, based on the size of said image data to form a brightness image, and outputs said brightness image; and an image composing means 456 that combines the color image formed in the fluorescent image computing means 455 and the brightness image formed in the reflectance image computing means 454 to form a composite image, and outputs said composite image.

Next, the operation of the fluorescent endoscope according to the current embodiment will be explained. First, the operation occurring when a composite image is to be displayed utilizing two autofluorescent images, each having a different wavelength band, will be explained.

Based on a signal outputted from a control computer 250, the semiconductor-laser power source 112 is activated and the excitation light Lr is emitted from the GaN semiconductor laser 111. The excitation light Lr emitted by the GaN semiconductor laser 111 is transmitted by an excitation light focusing lens 113 and enters the light guide 151b, and after being guided to the distal end of the endoscope insertion portion 150, said excitation light Lr is projected from the illuminating lens 153 onto the target subject 9. The autofluorescent image formed of the autofluorescent light emitted from the target subject 9 upon the irradiation thereof by the excitation light Lr is focused by the focusing lens 155, transmitted by the excitation light cutoff filter 154, enters the distal end of the image fiber 152, and enters the collimator lens 351 via the image fiber 152. The excitation light cutoff filter 154 is a long-pass filter for passing all light having a wavelength of 420 nm or longer. Because the wavelength of the excitation light is 410 nm, the excitation light reflected from the target subject 9 is cutoff by this excitation light cutoff filter 154. The autofluorescent image transmitted by the collimator lens 351 is perpendicularly reflected by the dichroic mirror 353. The autofluorescent image perpendicularly reflected by the dichroic mirror 353 is transmitted at a transmittance rate of 50% and reflected at a reflectance rate of 50% by the half mirror 354. The autofluorescent image transmitted by the half mirror 354 is perpendicularly reflected by the narrow-band fluorescent image mirror 355. The reflected image transmitted by the dichroic mirror 353, the autofluorescent image reflected by the half mirror 354, and the autofluorescent image reflected by the narrow-band fluorescent image mirror 355 enter the imaging optical system 356 together. At this time, the autofluorescent image that enters the imaging optical system 356 first is transmitted thereby at a 1:1 magnification rate. The autofluorescent image transmitted by the imaging optical system 356 at a 1:1 magnification rate is focused by the wide-band fluorescent image lens 358, and the autofluorescent image transmitted by the wide-band fluorescent image lens 358 is transmitted by the wide-band band pass filter 360, and obtained by the wide-band fluorescent image high-sensitivity obtaining element 363. The autofluorescent image reflected by the narrow-band fluorescent image mirror 355 is focused by the narrow-band fluorescent image lens 359, transmitted by the narrow-band band pass filter 361, and obtained by the narrow-band fluorescent image high-sensitivity obtaining element 364.

The autofluorescent images obtained by the wide-band fluorescent image high-sensitivity obtaining element 363 and the narrow-band fluorescent image high-sensitivity obtaining element 364 are converted to image signals that are electrical signals, and each is read out, based on a control signal from the readout means 368, as an image signal, respectively. Then, the image signal read out from the wide-band fluorescent image high-sensitivity obtaining element 368 is inputted to the AD converter 366 and digitized thereby, after which said digitized signal is stored in the wide-band fluorescent image memory 452. The image signal read out from the narrow-band fluorescent image high-sensitivity obtaining element 364 is inputted to the AD converter 366 and digitized thereby, after which said digitized signal is stored in the narrow-band fluorescent image memory 453.

Here, after the initially obtained autofluorescent image has been stored in the wide-band fluorescent image memory 452 and the narrow-band fluorescent image memory 453, in the same manner as occurred in the first embodiment, the image data of the region of interest thereof is outputted to the statistical quantity computing means 370. Then, after the image data of the region of interest outputted to the statistical quantity computing means 370 has been bit shifted to data containing 8 bits or less by the bit shifting means 371, the statistical quantity computing means 370 performs, in the same manner as occurred in the first embodiment, computational processing to determine the mean value thereof; after which, this mean value is then outputted to the magnification rate control means 369, and the magnification rate control means 369 determines, according to said mean value, the magnification rates of the autofluorescent image and the reflectance image, and outputs a control signal to the imaging optical system 356 and the reflectance image imaging optical system 507 so as to cause the magnification rates thereof to become said determined magnification rate.

Then, the next autofluorescent image passes through the imaging optical system 356, of which the magnification rate has been caused to be an appropriate magnification rate based on the magnification rate control signal from the magnification rate control means 369, and is obtained. Further, the magnification rate control means 369 outputs the drive range corresponding to the valid region occurring within the region of interest to the readout means 368, and the readout means 314 reads out the image data, corresponding to the drive range of said valid region, of the narrow-band fluorescent image high-sensitivity obtaining element 364, the wide-band fluorescent image high-sensitivity obtaining element 363, and the reflected image obtaining element 365. This range of the valid region is the region that is desired to be displayed as an image, and can be a preset region or a region set by use of a predetermined input means (not shown). Further, for cases in which the narrow-band fluorescent image high-sensitivity obtaining element 364 and the wide-band fluorescent image high-sensitivity obtaining element 363 are CCDs, the readout means 368 carries out the readout by the concurrent horizontal/vertical signals thereof and a standard clock signal, and the control of the drive range of the valid region is carried out by the change of the frequency of the concurrent horizontal/vertical signals thereof and the standard clock signal. The image data of the drive range corresponding to the valid region that has been readout is stored in the narrow-band fluorescent image memory 453, the wide-band fluorescent image memory 452, and the reflected image memory 451.

Then, the fluorescent image computing means 455 subjects the narrow-band fluorescent image of the valid range stored in the narrow-band fluorescent image memory 453 and the wide-band fluorescent image of the valid range stored in the wide-band fluorescent image memory 452 to computational processing according to the comparative ratio between the corresponding pixel values thereof to obtain a computed value for each pixel, assigns a color data to each computed value, and forms and outputs an image signal having color data. On the other hand, the reflected image computing means 454 assigns brightness data to the reflected image of the valid range stored in the reflected image memory 451, corresponding to the size of the signal thereof, and forms and outputs an image signal that has brightness data. Then, the color image signal outputted from the fluorescent image computing means 455 and the brightness image outputted from the reflected image computing means 454 are combined by the image composing means 456 to form a composite image, which is then outputted. The composite image outputted from the image composing means 456 is DA converted by the video signal processing circuit 506, and then inputted to the monitor 600 and displayed thereon as a composite image. It becomes possible to determine whether a tissue is a diseased tissue or a normal tissue based on the difference in the colors appearing in this composite image.

The operation occurring when a reflectance image is to be displayed is the same as that occurring in the first embodiment.

The series of operations relating to the displaying of a composite image and the displaying of a reflectance image are controlled by the control computer 200. Further, the operation for switching between the composite image display mode and the reflectance image display mode is performed by depressing the footswitch 2.

According to the fluorescent endoscope apparatus implementing the fluorescent image obtaining apparatus of the present invention: the statistical quantity computing means 370 computes the statistical quantity of the image signal of a predetermined region of a fluorescent image; and because the magnification rate control means 369 controls, based on the computed statistical quantity, the magnification rate of the imaging optical system 356 so as to determine the size of the fluorescent image and the size of the reflected image, in addition to the effects obtained according to the above-described first embodiment, the size of the reflected image can be caused to correspond to the size of the fluorescent image, and even for cases in which the fluorescent image and the reflected image are utilized in performing image computations, appropriate interimage processing can be carried out.

Further, according to the first and second embodiments, although the magnification rate control means is a means for controlling, based on the statistical quantity computed by the statistical quantity computing means, the magnification rate, in actuality, diagnosis can be easily performed by any user, and it is difficult to control the magnification rate to a preferred magnification rate. Accordingly, the provision of a statistical quantity computing means can be foregone, and an external input means such as a control knob or a foot switch, by use of which a user can conveniently control the magnification rate, can be provided in place thereof. The user can enlarge or reduce an image based on the brightness or flicker of said image: if the target-subject image is dark or has a lot of flicker, the user can operate said input means so that said target-subject image is reduced; if the target-subject image is bright and has little flicker, the user can operate said input means so that said target-subject image is enlarged. Then, the image data of the valid range can be read out in the same manner as occurred in the first and second embodiments.

Still further, according to the first and second embodiments, although the image corresponding to the valid region is displayed on the monitor 600, that is, the magnification rate of image displayed on the monitor 600 has been controlled by the magnification rate control means so that said image is reduced or enlarged accordingly, a display magnification rate control means can be provided, and the display magnification rate controlled so that the size of the image displayed on the monitor 600 is always the same. By controlling the magnification rate in this way, even for cases in which the image has been reduced by the magnification rate control means, by enlarging the displayed image, by use of the display magnification rate control means, the visual clarity of the image can be ensured. Further, a predetermined switch may be operated to switch between a case in which the display image is enlarged or reduced under control of the magnification rate control means, and a case in which the image is always displayed at the same size.

In addition, according to the first and second embodiments, although the statistical quantity based on the data of the autofluorescent image has been computed by the statistical computing means, the statistical quantity can be computed based on the data of the reflected image.

Additionally, according to the first and second embodiments, although the statistical quantity of the image data has been computed from the image data itself, the present invention is not limited thereto; for example, the Y signal converted to when an image is displayed (the Y of the YIQ of an NTSC signal, the Y of a YCbCr, etc.), can be utilized in computing the statistical quantity. Alternatively, for cases in which brightness data has been assigned to the image signal of a reflected image, the aforementioned statistical quantity can be computed from said brightness data.

Further, according to the first and second embodiments, although the readout means is a means for reading out only the image signal of the valid range by controlling, based on a control signal from the magnification rate control means, the drive range of each obtaining element, as a variation on this embodiment, the readout means can be a means for reading out the entire image signal obtained by each obtaining element, and then controlling, based on a control signal from the magnification control means, each obtaining element so that when the image data is to be stored in the wide-band fluorescent image memory, the narrow-band fluorescent image memory, the reflected image memory, and the reflectance image memory, only the image data of the valid range is stored.

Figure 4:
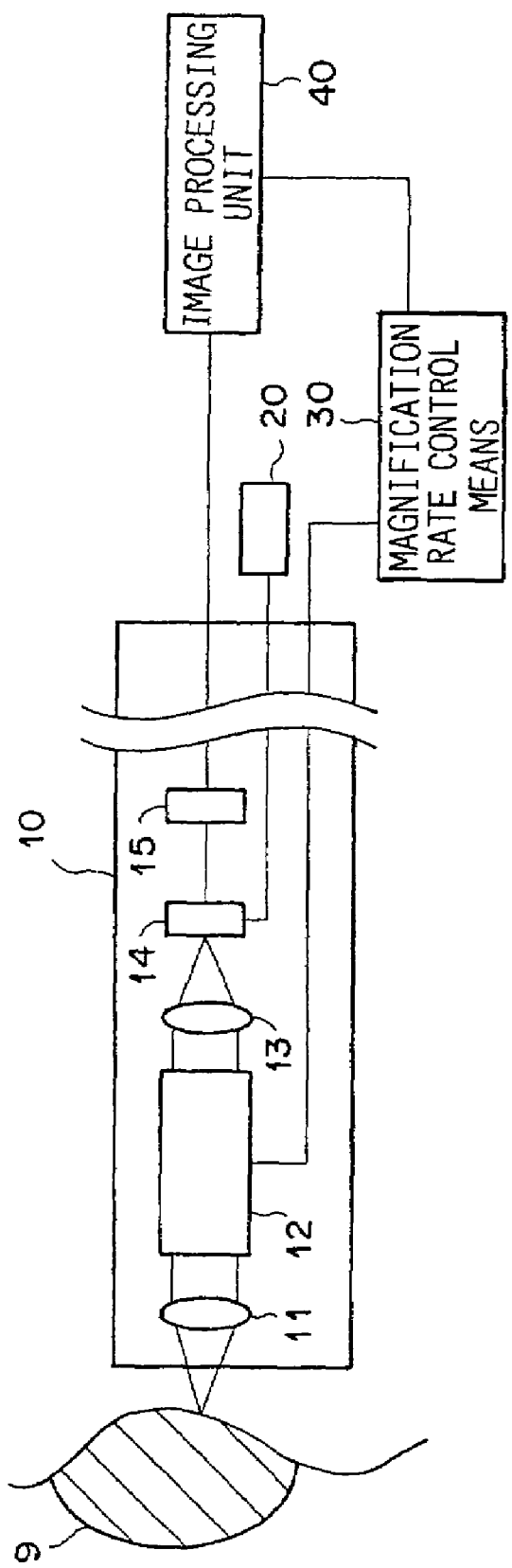
FIG. 4 is a schematic drawing of a portion of another embodiment of the fluorescent image obtaining apparatus according to the present invention.

Still further, according to the first and second embodiments, although a configuration has been adopted wherein the imaging optical system, the obtaining element, the AD converter, and the readout means are provided within the image processing portion, as an alternative configuration, the imaging optical system 12, the obtaining element 14, and the AD converter can be provided within the endoscope insertion portion 10, as shown in FIG. 4. Note that according to the embodiment shown in FIG. 4, the endoscope insertion portion 10 comprises: a focusing lens 11 that focuses a autofluorescent image, a reflected image, and a reflectance image, an imaging optical system 12, a focusing lens 13 that focuses the autofluorescent image, the reflected image, and the reflectance image; an image obtaining element 14, and an AD converter 15; wherein a control signal is outputted from the magnification rate control means 30 to the imaging optical system 12 and the image computing unit 40, so that when the image data is to be stored in the wide-band fluorescent image memory, the narrow-band fluorescent image memory, and the reflected image memory provided within the image computing unit, only the image data of the valid range is stored, based on the control signal from the magnification rate control means 30.

Figure 5:
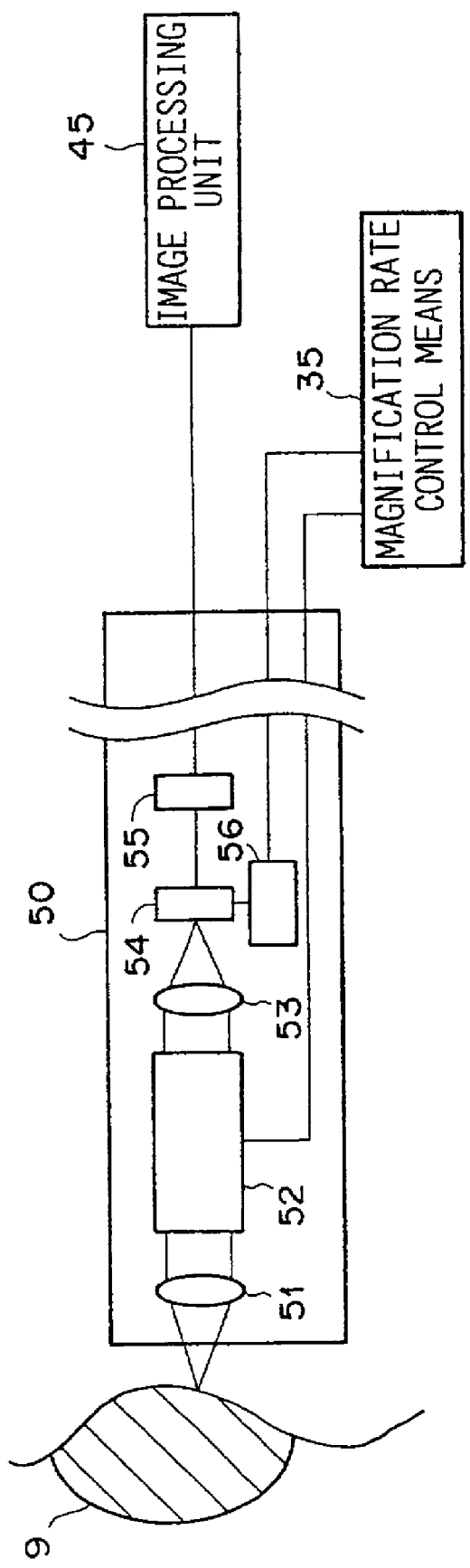
FIG. 5 is a schematic drawing of a portion of another embodiment of the fluorescent image obtaining apparatus according to the present invention.
Figure 6:
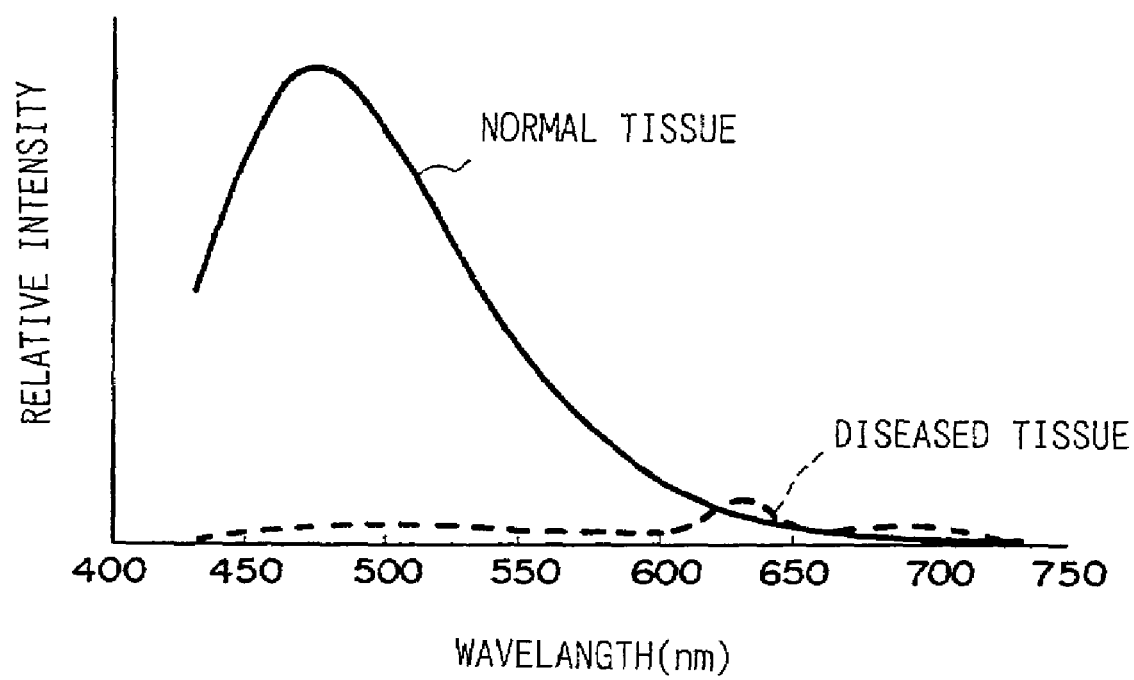
FIG. 6 is a graph illustrating the intensity distribution of the fluorescent light spectra of a normal tissue and of a diseased tissue.

In addition, as shown in FIG. 5, a configuration wherein the imaging optical system 52, the obtaining element 54, the AD converter 55 and the readout means 56 are disposed in the endoscope insertion portion 50 can also be adopted. Note that the embodiment shown in FIG. 5, the endoscope insertion portion 50 comprises: a focusing lens 51 for focusing a autofluorescent image, a reflected image, and a reflectance image, an imaging optical system 52, a focusing lens 53 for focusing the autofluorescent image, the reflected image, and the reflectance image; an image obtaining element 54, and an AD converter 55, and a readout means 56; wherein a control signal is outputted from the magnification rate control means 35 to the imaging optical system 52 and the readout means 56. The operation occurring for each procedure is the same as that occurring in the first and second embodiments described above.

Further, according to the first and second embodiments, although a configuration has been adopted wherein the fluorescent image obtaining element and the reflectance image obtaining element have been provided separately, both of said obtaining elements can be provided as an integrated obtaining element. Further, according to the second embodiment, the reflected image obtaining element can also be provided in the integrated obtaining element. In this case, the obtainment of each image can be switched in a temporal series manner, and by providing a mosaic filter on the surface of the obtaining element, the autofluorescent image, the reflectance image and the reflected image can be separated and obtained.

Still further, the magnification rate control means according to the first and second embodiments can be provided within a control computer.

In addition, although the imaging optical system according to the first and second embodiments has been provided in a configuration wherein the fluorescent image and reflected image imaging optical system and the reflectance image imaging optical system are provided separately, the fluorescent image and reflected image imaging optical system and the reflectance image imaging optical system can be provided in an integrated unit.

Note that according to the first and second embodiments, the magnification rate of the reflectance image has been matched to the fluorescent image in order to facilitate the smooth correlation of the reflectance image and the fluorescent image; however, the reflectance image can be set at a fixed, high magnification rate. In this case, a high-resolution reflectance image can be obtained. Further, the magnification rate of the reflectance image can be left unchanged, and only the magnification rate of the fluorescent image changed.

What is claimed is:

1. A fluorescent image obtaining apparatus comprising
   an illuminating means that guides an excitation light to a measurement area and illuminates the measurement area with the excitation light,
   an image obtaining means that obtains a fluorescent image with an image obtaining element based on the fluorescent light emitted from the measurement area upon the illumination thereof by the excitation light and which has been passed through an imaging optical system, and
   a readout means that reads out an image signal based on the fluorescent image obtained by the image obtaining means, further comprising
   a statistical quantity computing means that computes a statistical quantity based on the image signal of a predetermined region of the fluorescent image obtained by the image obtaining means, wherein
   the image obtaining means is provided with a magnification control means that determines the size of the fluorescent image by controlling, based on the statistical quantity, the magnification rate of the imaging optical system, and
   the magnification control means sets the magnification rate to cause the size of the autofluorescence image to be reduced when the statistical quantity is smaller than a predetermined value and sets the magnification rate to cause the size of the autofluorescence image to be increased when the statistical quantity is larger than the predetermined value.

2. A fluorescent image obtaining apparatus as defined in claim 1, further comprising
   an image processing means that subjects the image signal read out by the readout means to a predetermined image processing, wherein
   said image processing means performs image processing on the image signal of a predetermined valid range.

3. A fluorescent image obtaining apparatus as defined in claim 2, further comprising
   a display means that displays a target-subject image based on the image signal read out by the readout means, wherein
   said display means is a means that displays a target-subject image based on the image signal of said predetermined valid range and which has been subjected to image processes by said image processing means.

4. A fluorescent image obtaining apparatus as defined in claim 3, further comprising
   a display magnification rate control means that controls the magnification rate so that the target-subject image based on the image signal of said predetermined valid range is displayed at a predetermined constant size.

5. A fluorescent image obtaining apparatus as defined in any of claims 2, 3 or 4, wherein
   said readout means is a means that reads out only the image signal of a predetermined valid range within the fluorescent image.

6. A fluorescent image obtaining apparatus comprising
   an illuminating means that guides an excitation light and an illuminating-light to a measurement area and illuminates the measurement area with the excitation light and the illuminating-light,
   an image obtaining means that obtains a fluorescent image with an image obtaining element based on the fluorescent light emitted from the measurement area upon the illumination thereof by the excitation light and a reflectance image based on the reflected-light reflected from the measurement area upon the illuminating thereof by the illuminating-light, which have been passed through an imaging optical system, and
   a readout means that reads out an image signal based on the fluorescent image and an image signal based on the reflectance image obtained by the image obtaining means, further comprising
   a statistical quantity computing means that computes a statistical quantity based on the image signal of a predetermined region of the fluorescent image obtained by the image obtaining means, wherein
   the image obtaining means is provided with a magnification control means that determines the size of the fluorescent image and the reflectance image by controlling, based on the statistical quantity, the magnification rate of the imaging optical system and
   the magnification control means sets the magnification rate to cause the size of the autofluorescence image to be reduced when the statistical Quantity is smaller than a predetermined value and sets the magnification rate to cause the size of the autofluorescence image to be increased when the statistical Quantity is larger than the predetermined value.

7. A fluorescent image obtaining apparatus as defined in claim 6, further comprising
   an image processing means that subjects the image signal read out by the readout means to a predetermined image processing, wherein
   said image processing means is a means that performs image processing on the image signal of a predetermined valid range within said fluorescent image and the image signal corresponding thereto within said reflectance image.

8. A fluorescent image obtaining apparatus as defined in claim 7, further comprising
   a display means that displays a target-subject image based on the image signal read out by the readout means, wherein
   said display means is a means that displays a target-subject image based on said image predetermined valid range within said fluorescent image and said reflectance image and which have been subjected to image processes by the image processing means.

9. A fluorescent image obtaining apparatus as defined in claim 8, further comprising
   a display magnification rate control means that controls the magnification rate so that said target-subject image based on the image signal of said predetermined valid region is displayed at a predetermined constant size.

10. A fluorescent image obtaining apparatus as defined in any of claims 7, 8 or 9, wherein
    the readout means is a means that reads out only the image signals of said predetermined valid range within said fluorescent image and said reflectance image.

11. A fluorescent image obtaining apparatus comprising
    an illuminating means that guides an excitation light and a reference-light to a measurement area and illuminates the measurement area with the excitation light and the reference-light,
    an image obtaining means that obtains a fluorescent image with an image obtaining element based on the fluorescent light emitted from the measurement area upon the illumination thereof by the excitation light and a reflected image with an image obtaining element based on the reflected-light reflected from the measurement area upon the illuminating thereof by the reference-light, which have been passed through an imaging optical system, and a readout means that reads out an image signal based on the fluorescent image and an image signal based on the reflected image obtained by the image obtaining means, further comprising a statistical quantity computing means that computes the statistical quantity based on the image signal of a predetermined region within the fluorescent image or the reflected image obtained by the image obtaining means, wherein the image obtaining means is provided with a magnification control means that determines the size of the fluorescent image and the reflected image by controlling, based on the statistical quantity, the magnification rate of the imaging optical system, and the magnification control means sets the magnification rate to cause the size of the autofluorescence image to be reduced when the statistical quantity is smaller than a predetermined value and sets the magnification rate to cause the size of the autofluorescence image to be increased when the statistical quantity is larger than the predetermined value.

12. A fluorescent image obtaining apparatus as defined in claim 11, further comprising an image processing means that subjects the image signal read out by the readout means to a predetermined image processing, wherein said image processing means is a means that performs image processing on the image signal of a predetermined valid range within said fluorescent image and the image signal corresponding thereto within said reflected image.

13. A fluorescent image obtaining apparatus as defined in claim 12, further comprising a display means that displays a target-subject image based on the image signal read out by said readout means, wherein said display means is a means that displays a target-subject image based on said image signals of said predetermined valid range within said fluorescent image and said reflected image and which have been subjected to image processes by the image processing means.

14. A fluorescent image obtaining apparatus as defined in claim 13, further comprising a display magnification rate control means for controlling the magnification rate so that the target-subject image based on the image signal of the predetermined valid region is displayed at a predetermined constant size.

15. A fluorescent image obtaining apparatus as defined in any of claims 12, 13 or 14, wherein the readout means is a means that reads out only the image signals of a predetermined valid range within said fluorescent image and said reflected image.

16. A fluorescent image obtaining apparatus comprising an illuminating means that guides an excitation light, a reference-light and an illuminating-light to a measurement area and illuminates the measurement area with the excitation light, the reference-light, and the illuminating-light, an image obtaining means that obtains with an image obtaining element a fluorescent image based on the fluorescent light emitted from the measurement area upon the illumination thereof by the excitation light, a reflectance image based on the reflected-light reflected from the measurement area upon the illuminating thereof by the illuminating-light, and a reflected image based on the reflected-light reflected from the measurement area upon the illuminating thereof by the reference-light, which have been passed through an imaging optical system, and a readout means that reads out an image signal based on the fluorescent image, an image signal based on the reflectance image, and an image signal based on the reflected image obtained by the image obtaining means, further comprising a statistical quantity computing means that computes a statistical quantity based on the image signal of a predetermined region within the fluorescent image or the reflected image obtained by the image obtaining means, wherein the image obtaining means is provided with a magnification control means that determines the size of the fluorescent image, the reflected image, and the reflectance image by controlling, based on the statistical quantity, the magnification rate of the imaging optical system, and the magnification control means sets the magnification rate to cause the size of the autofluorescence image to be reduced when the statistical quantity is smaller than a predetermined value and sets the magnification rate to cause the size of the autofluorescence image to be increased when the statistical quantity is larger than the predetermined value.

17. A fluorescent image obtaining apparatus as defined in claim 16, further comprising an image processing means that subjects the image signal read out by the readout means to a predetermined image processing, wherein said image processing means is a means that performs image processing on the image signal of a predetermined valid range within said fluorescent image and the respective image signals corresponding thereto within said reflected image and said reflectance image.

18. A fluorescent image obtaining apparatus as defined in claim 17, further comprising a display means that displays a target-subject image based on the image signal read out by the readout means, wherein said display means is a means that displays a target-subject image based on the aforementioned image signals of said predetermined valid range within said fluorescent image, said reflected image, and said reflectance image and which have been subjected to image processes by the image processing means.

19. A fluorescent image obtaining apparatus as defined in claim 18, further comprising a display magnification rate control means that controls the magnification rate so that the target-subject image based on the image signal of the predetermined valid region is displayed at a predetermined constant size.

20. A fluorescent image obtaining apparatus as defined in any of claims 17, 18 or 19, wherein the readout means is a means that reads out only the image signals of a predetermined valid range of the fluorescent image, the reflected image, and the reflectance image.

21. A fluorescent image obtaining apparatus as defined in any of claims 1, 2, 3, 4, 6, 7, 8 or 9, wherein
the predetermined region is the entirety of the fluorescent image, and the statistical quantity computing means computes the statistical quantity of the image signal of the entire said image.

22. A fluorescent image obtaining apparatus as defined in any of claims 11, 12, 13, 14, 16, 17, 18, or 19, wherein
the predetermined region is the entirety of either the fluorescent image or the reflected image, and the statistical quantity computing means computes the statistical quantity of the image signal of the entirety of either of said images.

23. A fluorescent image obtaining apparatus as defined in any of claims 1, 2, 3, 4, 6, 7, 8 or 9, wherein
the predetermined region is the region of interest of the fluorescent image, and the statistical quantity computing means computes the statistical quantity of the image signal of said region of interest of said image.

24. A fluorescent image obtaining apparatus as defined in any of claims 11, 12, 13, 14, 16, 17, 18, or 19, wherein
the predetermined region is the region of interest of the fluorescent image or the reflected image, and the statistical quantity computing means computes the statistical quantity of the image signal of said region of interest of either of said images.

25. A fluorescent image obtaining apparatus as defined in any of claims 1,2,3,4,6,7,8,9, 11, 12, 13, 14, 16, 17, 18, or 19, wherein
the statistical computing means is a means that performs a weighted computation on a predetermined range corresponding to the degree of interest thereof, and computing the statistical quantity of the computed image signal obtained thereby.

26. A fluorescent image obtaining apparatus as defined in any of claims 1,2,3,4,6,7,8,9, 11, 12, 13, 14, 16, 17, 18, or 19, wherein
the statistical quantity of the image signal consists of at least one of the following: the maximum value, the minimum value, the mean value, the combination of the maximum value and the standard deviation, the combination of the minimum value and the standard deviation, the combination of the mean value and the standard deviation, wherein
when any of said maximum value, minimum value, or average value of the statistical quantity is small, the magnification rate is caused to be small, and when any of said values is large, the magnification rate is caused to be large.

27. A fluorescent image obtaining apparatus as defined in any of claims 1,2,3,4,6,7,8,9, 11, 12, 13, 14, 16, 17, 18, or 19, wherein
the readout means controls the readout frequency in accordance with the predetermined valid range.

28. A fluorescent image obtaining apparatus as defined in any of claims 1,2,3,4,6,7,8,9, 11, 12, 13, 14, 16, 17, 18, or 19, wherein
a bit shifting means is provided that shifts, if the pixel data based on the image signal is represented by data constituted of 9 bits or more, the number bits constituting the data representing the pixel data based on the image signal so that the number of bits there of is 8 or less, and the statistical quantity computing means is a means that computes the statistical quantity based on the bit-shifted data.

29. A fluorescent image obtaining apparatus as defined in any of claims 1,2,3,4,6,7,8,9, 11, 12, 13, 14, 16, 17, 18, or 19, wherein
a portion or the entirety of the illuminating means, the image obtaining means, and the readout means is provided in the form of an endoscope provided with an insertion portion to be inserted into a body cavity of a patient.

30. A fluorescent image obtaining apparatus as defined in any of claims 1,2,3,4,6,7,8,9, 11, 12, 13, 14, 16, 17, 18, or 19, wherein
a portion or the entirety of the illuminating means, the image obtaining means, and the readout means are disposed within the insertion portion, and
the portions of the illuminating means, the image obtaining means, and the readout means other than those portions disposed within the insertion portion are disposed within a processor section,
wherein the imaging optical system for controlling the aforementioned magnification rate is disposed as a magnification rate control means within the processor section.

31. A fluorescent image obtaining means as defined in any of claims 1,2,3,4,6,7,8,9, 11, 12, 13, 14, 16, 17, 18, or 19, wherein
a portion or the entirety of the illuminating means, the image obtaining means, and the readout means are disposed within the insertion portion, and the portions of the illuminating means, the image obtaining means, and
the readout means other than those portions disposed within the insertion portion are disposed within a processor section, wherein
the imaging optical system for controlling the aforementioned magnification rate is disposed as a magnification rate control means within the insertion portion.

32. A fluorescent image obtaining apparatus as defined in claim 1, wherein the statistical quantity is computed based on a plurality of weighted image data from a corresponding plurality of regions within the predetermined region.

33. A fluorescent image obtaining apparatus as defined in claim 32, wherein a first region having a highest degree of interest is weighted more than a second region having a high degree of interest.

34. A fluorescent image obtaining apparatus as defined in claim 33, wherein the first region is disposed at about a center of the predetermined region.

* * * * *